(12) United States Patent
Allen

(10) Patent No.: US 6,587,542 B1
(45) Date of Patent: **\*Jul. 1, 2003**

(54) DENTAL PANORAMIC IMAGING SYSTEM

(75) Inventor: Brian Philip Allen, Halstead (GB)

(73) Assignee: EEV Ltd., Chelmsford (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/875,987

(22) PCT Filed: Feb. 8, 1996

(86) PCT No.: PCT/GB96/00279

§ 371 (c)(1),
(2), (4) Date: Oct. 6, 1997

(87) PCT Pub. No.: WO96/25880

PCT Pub. Date: Aug. 29, 1996

(51) Int. Cl.[7] .............................................. H05G 1/64
(52) U.S. Cl. ....................................... 378/98.8; 378/38
(58) Field of Search ............................ 378/22, 38, 39, 378/40, 98.8

(56) References Cited

U.S. PATENT DOCUMENTS

| 4,995,062 A | * | 2/1991 | Schulze-Ganzlin et al. .. 378/40 X |
| 5,214,686 A | * | 5/1993 | Webber ........................ 378/38 |
| 5,600,699 A | * | 2/1997 | Suzuki et al. .................. 378/38 |

FOREIGN PATENT DOCUMENTS

| EP | 0357944 | 3/1990 |
| EP | 0685201 | 12/1995 |
| WO | 9014793 | 12/1990 |

* cited by examiner

Primary Examiner—Robert H. Kim
Assistant Examiner—Jurie Yun

(57) ABSTRACT

An imaging system for producing a panoramic radiograph of a patient's jaw for dental analysis includes an X-ray source (2) carried at one end of an arm (1) and detector means (7) at the other end. The front surface of the detector means (7) carries scintillator material (8) which substantially solely defines the area of the detector means at which the image information is captured. The secondary diaphragm or slot used in conventional panoramic X-ray imaging systems can thus be omitted, giving a less complicated system.

8 Claims, 1 Drawing Sheet

DENTAL PANORAMIC IMAGING SYSTEM

Figure 1:
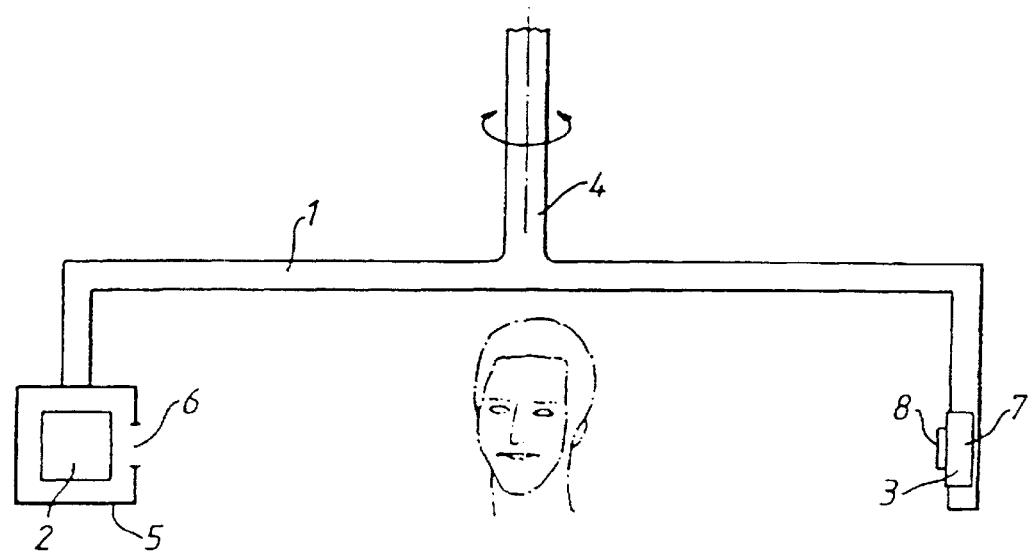

This invention relates to imaging systems and more particularly to systems suitable for dental X-ray diagnosis where the system may be used to produce panoramic radiographs of the jaw of a patient.

In conventional dental X-ray systems for producing panoramic radiographs, an X-ray source is directed at the patient and an image recorded on a moving X-ray film. A secondary diaphragm having a slot is located in front of the X-ray film as an aperture to define the part of the film where the radiation-is incident. It has previously been proposed to replace the moving X-ray film by a CCD sensor. In this system, a unit is used which is rotatable about a vertical axis and which carries an X-ray source at one end of an arm and a CCD sensor at the other end of the arm located behind a secondary diaphragm. The secondary diaphragm includes an opening or secondary slot which acts as the aperture.

According to a first aspect of the invention, there is provided an imaging system for dental use comprising: a source of X-ray radiation; solid state detector means having a radiation sensitive region which includes an image area at which charge accumulates which is representative of incident radiation, the extent of the image area being defined substantially solely at the detector means: means for moving the source and detector means relative to a subject to be examined, in which the subject is arranged to be located between them and means for processing the output of the detector means to obtain a panoramic image of the subject.

The inventor has realised that the secondary slot previously considered to be an essential feature may be eliminated from the system without causing image quality deterioration to such an extent that it is no longer satisfactory and in certain cases that elimination of the secondary slot may improve image quality.

The image area is defined substantially solely at the detector means and obviates the need for a secondary slot or opening in a diaphragm to be used to define the aperture area as required in the conventional moving X-ray film arrangement or the previously proposed CCD sensor systems. This produces a more simplified system compared to previously known arrangements which is less bulky and allows for more precise control of the alignment and movement of the arrangement, improving reliability. Also, use of the invention facilitates assembly and eases design constraints. In some situations a secondary slot may be responsible for generating scattered radiation which degrades the image. Elimination of the slot by employment of the invention can thus improve image quality.

In one advantageous embodiment of the invention, the detector means includes scintillator material carried on its surface for converting X-ray radiation into radiation of another wavelength for detection by said detector means and the image area is defined at the detector means by the extent of the scintillator material on the detector means. The scintillator material which converts incident X-ray radiation into a wavelength to which the detector means is responsive may be carried directly by the surface of the detector means or on an intermediate layer laid down on the detector means.

In another advantageous embodiment of the invention, the extent of the image area is defined by the location of charge storage means at which radiation is incident to cause the accumulation of charge. Thus, where the detector means is a CCD sensor array, the location of charge storage sites defines the image area. Scintillator material may be used on the CCD array in register with it to further define the image area extent or could alternative extend beyond the charge storage sites in one or more directions.

It may be advantageous in some embodiments in accordance with the invention to include shielding material on the surface of detector means surround in the scintillator material to absorb stray X-ray radiation. Preferably the solid state detector means is a CCD array but other types of sensor may be used.

According to a second aspect of the invention, an imaging system for dental use comprises a source of X-ray radiation; solid state detection means having a radiation sensitive region which includes an image area: means for moving the source and detector means relative to a subject to be examined, the subject being arranged to be located between them: and means for processing an output of the detector means to obtain a panoramic image of the subject, and wherein no secondary slot is located in front of the detector means.

According to a feature of the invention, there is provided solid state detector means for use in an imaging system in accordance with the invention.

Figure 2:
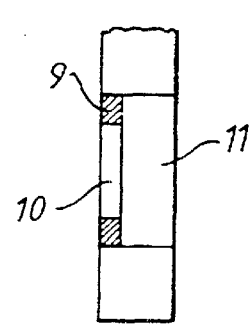
Figure 3:
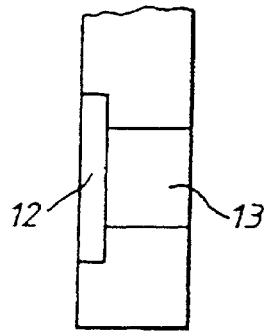

Some ways in which the invention may be performed are now described by way of example with reference to the accompanying drawing in which:

FIG. 1 schematically illustrates a dental X-ray arrangement in accordance with the invention; and FIGS. 2 and 3 schematically show alternative detector means for the arrangement of FIG. 1.

With reference to FIG. 1, an X-ray system for producing radiographs of a patient's jaw includes an arm 1 carrying an X-ray source 2 at one end and a detector arrangement 3 at the other end. At the mid-point of the arm 1 a shaft 4 is vertically extensive and in use is located over the patient's head and rotates as shown by the arrows about its longitudinal axis. The X-ray source 2 is located within a housing 5 having a slot 6 to define a beam of X-ray radiation and is adjusted in position so that the radiation is incident on the patient's jaw. After passing through the jaw the attenuated X-ray radiation is then incident at the detector 3. The detector 3 includes a CCD sensor array 7 having a layer of scintillator material 8 laid down on its surface at which the X-ray radiation is received. The scintillator material 8 is of a configuration which corresponds to the slot 6 in the housing 5 of the X-ray source and the extent of the material 8 defines the image area. As the arm 1 is rotated about the axis X-X of the shaft 4, different regions of the patient's jaw are irradiated and imaged by the CCD sensor array 7. The image information produced at the sensor array 7 is clocked out at an appropriate rate to produce the required panoramic image. This may be stored for later analysis and/or displayed on a VDU.

In another detector means, as shown in FIG. 2, shielding material 9 is arranged around scintillator material 10 to absorb any X-rays incident on the CCD detector array 11 outside the scintillator material 10.

In another arrangement, as shown in FIG. 3, scintillator material 12 covers an area larger than that defined by the slot in the X-ray housing and extends beyond the radiation sensitive region of the CCD detector array 13. In this embodiment the radiation sensitive region defines the image area of the X-ray system.

What is claimed is:

1. An imaging system for dental use comprising: a source of X-ray radiation; solid state detector means having a radiation sensitive region which includes an image area at which charge accumulates which is representative of incident radiation;- scintillator material carried on the surface of said image area for converting X-ray radiation into radiation of a different wave length for detection by said detector means, there being no secondary diaphragm or slot serving as an aperture in said system to define said image area; means for moving said source and said detector means relative to a subject to be examined, in which the subject is arranged to be located between them; and means for processing the output of said detector means to obtain a panoramic image of the subject.

2. A system as claim 1 wherein said image area being defined at said detector means by the extent of said scintillator material on the detector means.

3. A system as claimed in claim 1 wherein the extend of the image area is defined by the location of charge storage means at which radiation is incident to cause the accumulation of charge.

4. A system as claimed in claim 1, wherein said solid state detector means is a CCD array.

5. A system as claimed in claim 1, wherein said image area is surrounded by shielding material for absorbing X-ray radiation incident on said detector means outside said image area, said shielding material and said detector means being carried on a common mount.

6. A system as claimed in claim 5 wherein said scintillator material and said shielding material lie in substantially the same plane.

7. A system as claimed in claim 1 wherein said X-ray source includes a diaphragm having a slot therein defining the configuration of the X-ray beam which irradiates a subject and wherein said image area is of substantially the same dimensions as said slot.

8. Solid state detection means for use in an imaging system in accordance with claim 1.

* * * * *